United States Patent [19]
Burris

[11] Patent Number: 5,834,937
[45] Date of Patent: Nov. 10, 1998

[54] BOLT HOLE PROBE WITH FLEXURE

[75] Inventor: Kirk Burris, Kent, Wash.

[73] Assignee: Zetec, Inc., Issaquah, Wash.

[21] Appl. No.: 721,467

[22] Filed: Sep. 27, 1996

[51] Int. Cl.$^6$ ................................................ G01N 27/90
[52] U.S. Cl. ........................... 324/219; 73/866.5; 324/262
[58] Field of Search ................................... 324/219–221, 324/262, 757, 758; 73/866.5; 165/11.1, 11.2

[56] References Cited

U.S. PATENT DOCUMENTS

| | | | |
|---|---|---|---|
| 3,676,776 | 7/1972 | Bauer et al. | 324/758 X |
| 3,831,084 | 8/1974 | Scalese et al. | 324/219 |
| 4,413,231 | 11/1983 | Amedro et al. | 324/220 |
| 4,629,984 | 12/1986 | Scalese | 324/219 X |
| 4,633,176 | 12/1986 | Reimer | 324/758 |
| 5,174,165 | 12/1992 | Pirl | 324/220 X |
| 5,279,168 | 1/1994 | Timm | 324/220 X |
| 5,517,124 | 5/1996 | Rhoades et al. | 324/662 |

*Primary Examiner*—Gerard R. Strecker
*Attorney, Agent, or Firm*—David L. Tingey

[57] ABSTRACT

An eddy current probe shaft with probe and drive mechanism attached for measuring integrity of a bolt hole, particularly useful for aircraft bolt holes, includes a continuous helical coil manufactured integrally into a one-piece steel shaft providing flexure in the shaft enabling axial self-alignment even when the shaft is inserted obliquely into a bolt hole. The intact, integrated helical coil of flexible steel provides a constant length probe, effectively noncompressible and nonelongatable, flexible under external bias and with a spring constant sufficient to reliably return the shaft to a straight-axis rest position upon release of the external bias. An eddy current probe with a test coil in a probe head is attached at the shaft distal end for measuring cracks and similar structural anomalies in the bolt hole. A drive mechanism is attached at the shaft proximal end for rotating the shaft and probe in the bolt hole for a circumferential scan of the bolt hole interior surface.

8 Claims, 1 Drawing Sheet

BOLT HOLE PROBE WITH FLEXURE

BACKGROUND

1. Field of the Invention

This invention relates to positioning shafts for nondestructive testing probes for inspecting structural anomalies and, specifically, to an eddy current probe in combination with a flexible shaft used in inspection of the interior of bolt holes of aircraft, the probe utilizing at least one wound coil for projecting an electromagnetic field into an adjoining material to be tested.

2. Prior Art

It is known in the art to have a remote sensor, such as an eddy current probe, attached to the lead end of a shaft for remotely obtaining nondestructive measurements of the integrity of aircraft bolt holes. An eddy current test coil is characteristically mounted radially on the probe proximate the probe circumference such that when the probe is inserted in a bolt hole and rotated, the coil circumferentially scans the bolt hole interior surface. Typically, the probe and shaft are rotated by a drive mechanism, or gun, to which the shaft is attached. As the shaft is rotated, the eddy current test coil in a probe head circumferentially scans the cylindrical bolt hole surface.

In using bolt hole probes, it is previously required that the probe be aligned with the hole axis to insure a reproducible measurement and that there is not excessive torque on the probe or shaft that may cause excessive wear, a mechanical break, crack or other physical damage to the probe head or shaft.

With unrestricted access to a bolt hole, it is possible to adequately align the probe manually. However, it is common in aircraft that bolt holes are poorly accessible, and a bolt hole cannot be approached normal to the surface in which the bolt hole is found. Thus, the hole must be approached obliquely with the probe urged into the hole off-normal followed by the shaft which is itself connected to the drive mechanism. Previously, the shaft and probe remain oblique within the hole, and the measurement and the probe itself are compromised. And even with unrestricted access to a bolt hole, it can be difficult for an inspecting technician to maintain alignment.

It is the object of the present invention to provide a flexible shaft to which an eddy current probe with its probe head and drive mechanism on distal and proximal ends respectively are attached for delivering the probe into an aircraft bolt hole coaxially even when the shaft is introduced to the bolt hole obliquely or becomes oblique during the inspection.

SUMMARY OF THE INVENTION

This objective is achieved in a probe including a single, continuous flexible helical coil manufactured into a shaft to which an eddy current probe is attached at the shaft distal end. The helical coil is integral with the shaft body, as opposed to a mounted helical coil mounted to the shaft, to assure inherent integrity and alignment in a shaft straight-axis rest position.

The shaft is manufactured of flexible steel, typically of grade 17-4PH H900, which is heat treated to obtain good flexibility while simultaneously providing an excellent spring constant and material durability. It is advantageous to use flexible steel over Nylon or Delrin materials or the like because of the spring constant. Other materials may offer flexibility, even perhaps better flexibility than steel, but they lack a sufficient spring constant and are susceptible to wear and failure after repeated stressing during rotation in use.

DETAILED DESCRIPTION OF THE PREFERRED EMBODIMENTS

Figure 1:
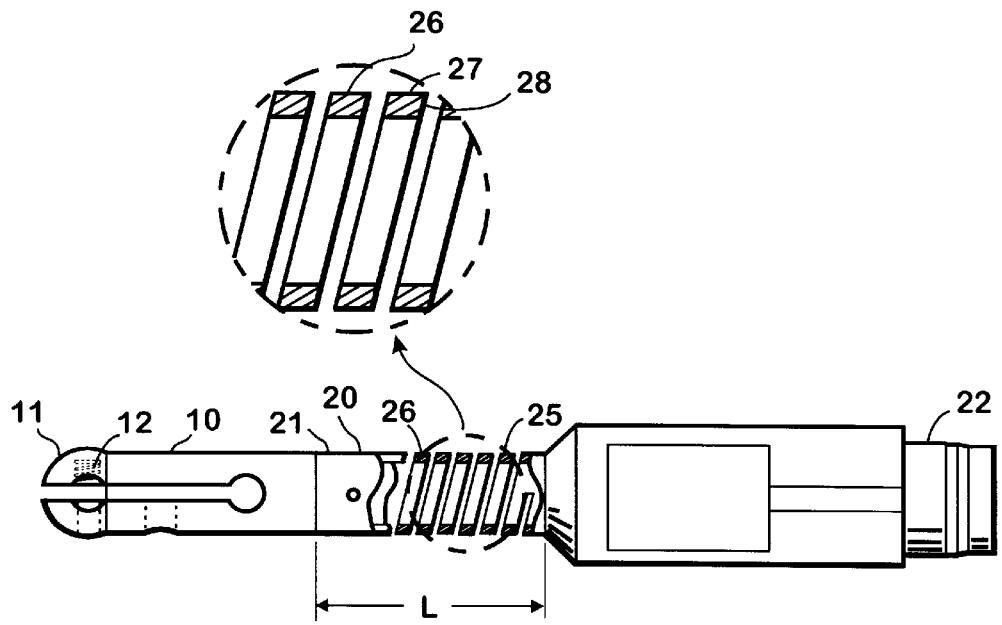
FIG. 1 is a side view of a probe attached to a shaft with a cut-away section of the helical coil.
Figure 2:
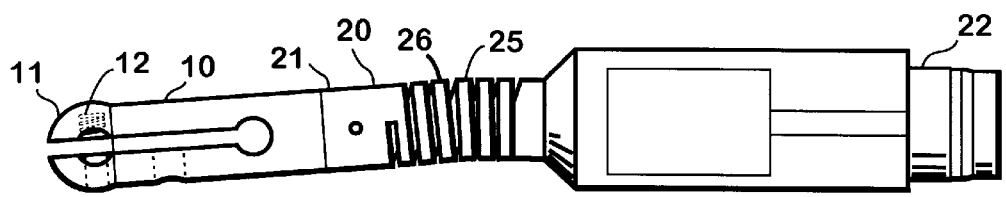
FIG. 2 is a side view of a probe attached to a shaft in flexure.
Figure 3:
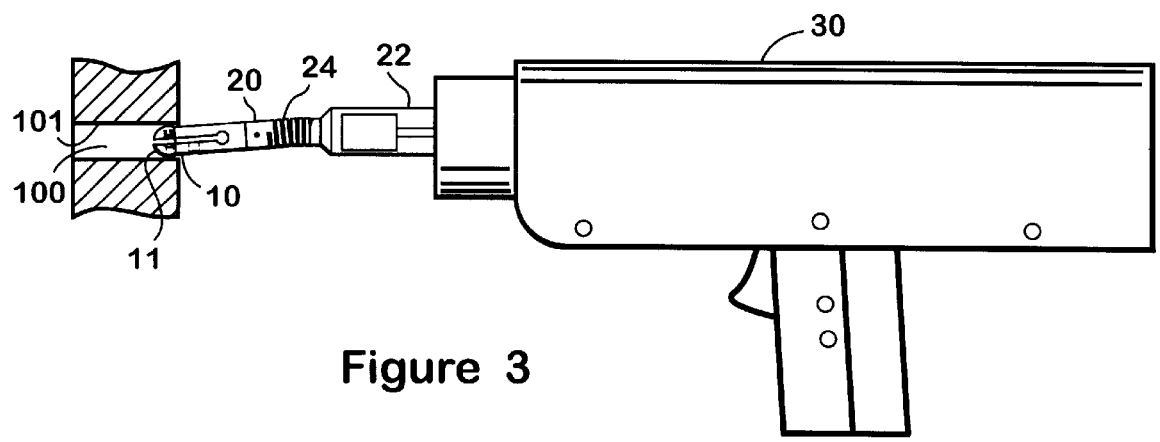
FIG. 3 is an illustration of the probe and flexible shaft attached to a drive mechanism in a typical application within a bolt hole.

The bolt hole probe and shaft of the present invention includes a probe 10, a tubular shaft 20 having a wall and a passageway therethrough and having distal and proximal ends, 21, 22, supporting the probe 10 on the shaft distal end 21 and a drive mechanism 30 on the shaft proximal end 22 for rotating the probe 10 in a bolt hole 100. For these purposes, probe distal end 21 is meant to describe the end first entering the bolt hole 100, and the probe proximal end 22 is meant to describe the drive mechanism end opposite the distal end 21.

The probe 10 typically comprises a probe head 11 including an eddy-current test coil means comprising at least one coil 12 nested in a probe head 11 as an inductor on the cylindrical probe 10 for generating eddy currents in a test material or structure. Because the probe 10 must be aligned in the bolt hole 100 to repeatedly and reliably measure defects and cracks and similar flaws in aircraft bolt holes, the probe head 11 is sized to match the interior of the intended bolt hole 100 for centering and aligning the probe in the bolt hole 100, thus bringing the test coil 12 into proximity with the test structure. The probe head 11 with test coil 12 may also be adjustable for small adaptations to match varying bolt hole sizes. The test coil 12 is electrically connected to an electronics package including an alternating current signal generator, data processor and analyzer (not shown).

Because, for lack of accessibility of a bolt hole 100, the probe 10 often must be inserted into the bolt hole 100 obliquely instead of normally as preferable for ease of alignment, the shaft 20 is also provided with a flexure 24 longitudinal in the shaft 20. Thus, the probe 10 may be inserted off-normal, relying on the probe head 11 to align the probe 10 in the hole 100 with the shaft flexure 24 allowing the shaft 20 to bend into alignment as directed by the probe head 11 even while the drive mechanism 30 remains oblique to the bolt hole 100.

To be structurally rigid sufficient to support the probe 10 in a shaft rest position without bending (straight axis) yet bendable upon application of external bias, the flexure 24 comprises a helical coil 25 formed of heat-treated steel, integral with the shaft 20. Simultaneous with the requirements of being bendable and self-supporting with a straight axis, the helical coil 25 also has a strong bending spring constant such that the shaft 20 returns to its rest position upon release of the external bias. Steel of grade 17-4PH H900 satisfies this requirement.

Likewise, the shaft 20 is of constant length, L, for measurement reproducibility, effectively noncompressible and nonelongatable longitudinally. Therefore, rather than employ a wound coil which would be compressible and elongatable, the shaft 20 is a one-piece tube into which is cut the helical coil 25 intermediate the tube. The one-piece shaft 20 is then wholly intact with the helical coil 25 integral in the shaft 20, in addition to maintaining constant length, providing durability and inherent integrity of assembly and self-alignment, and shaft nondistortion.

The helical coil 25 is defined then by a helical member 26 tracing the coil helix defined by a helical groove around the tube wall and through to the passageway therein forming said coil in the tube coaxial in the shaft cut into the one-piece shaft 20. The member 26 is typically of substantially rectangular cross-section. The width 27 of the helical member 26 is longitudinal with the shaft 20 and of dimension less than the depth 28 which is radial with the shaft 20 to facilitate bending flexure while resisting coil longitudinal elongation and compression.

One skilled in the art will recognize the advantages taught by this invention and illustrated by the preferred embodiment presented. The specification and drawings are not intended to represent an exhaustive description of the invention. Obvious applications and extensions of the invention are intended to be within the spirit and scope of this invention.

I claim:

1. A flexible bolt hole probe shaft having distal and proximal ends for supporting both a probe on the shaft distal end and a drive mechanism on the shaft proximal end, and including flexure means longitudinal in the shaft with structural rigidity sufficient to support the probe in a shaft rest position without bending yet bending upon application of external bias and returning to its rest position upon release of the external bias, the improvement comprising said shaft including a rigid, noncompressible, nonextendable tube to which said probe is attached, said tube having a tube wall and a passageway therethrough, and a helical coil noncompressible and nonelongatable in use with said probe defined by a helical groove around the tube wall and through to the passageway therein forming said coil in the tube coaxial in the shaft.

2. The flexible bolt hole probe of claim 1 further comprising means for facilitating bending flexure in said coil while preventing coil longitudinal elongation and compression.

3. The flexible bolt hole probe of claim 2 in which the means for facilitating bending flexure in said coil while preventing coil longitudinal elongation and compression comprises said coil including a helical member with a noncircular cross-section.

4. The flexible bolt hole probe of claim 3 in which the means for facilitating bending flexure in said coil while preventing coil longitudinal elongation and compression comprises a helical member in said coil with a substantially rectangular cross-section with a width and a depth in which the width of the helical member with a substantially rectangular cross-section is longitudinal with the shaft and of dimension less than the depth which is radial with the shaft.

5. The combination of a generally rigid tubular probe shaft including a tubular wall and a passageway therethrough, said shaft having distal and proximal ends and a probe attached to the shaft distal end and a drive mechanism connected to the shaft proximal end for rotating the shaft, the combination comprising, flexure means in the generally rigid tubular probe shaft for bending of the shaft, detection means in the probe disposed radially for detecting from the probe circumference.

6. The combination of claim 5 in which the detection means comprises at least one eddy current test coil on a probe attached to the probe shaft with the eddy current test coil disposed radially from the probe with a coil end near the probe circumference such that the coil end presents itself in near contact with a bolt hole interior surface in which the probe may be placed.

7. The combination of claim 5 in which the flexure means comprises a helical coil.

8. The combination of claim 5 in which the flexure means comprises said shaft including a rigid, noncompressible, nonextendable tube to which said probe is attached, said tube having a tube wall and a passageway therethrough, and a helical coil noncompressible and nonelongatable in use with said probe defined by a helical groove around the tube wall and through to the passageway therein forming said coil in the tube coaxial in the shaft.

* * * * *